US007261915B2

(12) United States Patent
Boulais et al.

(10) Patent No.: US 7,261,915 B2
(45) Date of Patent: Aug. 28, 2007

(54) ELECTROHYDRODYNAMIC COATING FLUID DELIVERY APPARATUS AND METHOD

(75) Inventors: Dennis R. Boulais, Danielson, CT (US); Eric B. Stenzel, Tuam (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 296 days.

(21) Appl. No.: 10/409,590

(22) Filed: Apr. 9, 2003

(65) Prior Publication Data

US 2004/0200729 A1 Oct. 14, 2004

(51) Int. Cl.
*B05D 1/04* (2006.01)

(52) U.S. Cl. ............... 427/2.28; 427/475; 427/483; 427/485

(58) Field of Classification Search ............... 427/2.24, 427/2.25, 2.28, 475–477, 483, 485, 486; 361/226; 118/620–636
See application file for complete search history.

(56) References Cited

U.S. PATENT DOCUMENTS

| 2,658,009 | A | * | 11/1953 | Ransburg ............... 427/483 |
| 4,264,641 | A | * | 4/1981 | Mahoney et al. ......... 427/483 |
| 5,279,863 | A | | 1/1994 | Escallon |
| 5,337,963 | A | * | 8/1994 | Noakes ................. 239/690 |
| 5,503,335 | A | * | 4/1996 | Noakes et al. ........... 239/690 |
| 6,669,980 | B2 | * | 12/2003 | Hansen ................. 427/2.24 |
| 2002/0007869 | A1 | | 1/2002 | Pui et al. |
| 2003/0003221 | A1 | | 1/2003 | Zhong et al. |
| 2003/0185964 | A1 | | 10/2003 | Weber et al. |
| 2003/0209005 | A1 | * | 11/2003 | Fenn .................. 60/203.1 |

FOREIGN PATENT DOCUMENTS

| EP | 1 010 468 A1 | 6/2000 |
| WO | WO 02/22181 A1 | 3/2002 |

\* cited by examiner

*Primary Examiner*—Fred J. Parker
(74) *Attorney, Agent, or Firm*—Kenyon & Kenyon LLP

(57) ABSTRACT

An apparatus and method for improved control of low viscosity fluid flow during electrohydrodynamic spray deposition of the fluid to coat small targets, such as medical devices like stents. The apparatus includes a target holder which applies a first electrical potential to a target, a coating fluid transporter such as a wick, a siphon tube or a siphon tube with a wick therein along which the coating fluid flows from a reservoir to a dispensing end of the transporter, and an electrode which applied a second electrical potential to the coating fluid sufficient to cause the coating fluid to be attracted from the dispensing end of the transporter toward the target. This provides a target coating apparatus with highly self-regulating coating fluid flow characteristics despite the low viscosity of the coating fluid, while producing highly consistent and uniform target coatings.

11 Claims, 4 Drawing Sheets

ELECTROHYDRODYNAMIC COATING FLUID DELIVERY APPARATUS AND METHOD

FIELD OF THE INVENTION

The present invention generally regards an apparatus and method for application of coatings to small devices, such as the application of therapeutic and protective coatings to stents. More specifically, the present invention pertains to an apparatus and method for improved control of very low viscosity coating fluid flow during electrohydrodynamic spray deposition of coatings onto targets such as medical stents.

BACKGROUND

Medical implants are used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, esophagus, trachea, colon, biliary tract, urinary tract, prostate, brain, and the like.

The term "therapeutic agent" as used herein includes one or more "therapeutic agents" or "drugs". The terms "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Coatings used with the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

In a preferred embodiment, the polymer used to coat the medical device is provided in the form of a coating on an expandable portion of a medical device. After applying the drug solution to the polymer and evaporating the volatile solvent from the polymer, the medical device is inserted into a body lumen where it is positioned to a target location. In the case of a balloon catheter, the expandable portion of the catheter is subsequently expanded to bring the drug-impregnated polymer coating into contact with the lumen wall. The drug is released from the polymer as it slowly dissolves into the aqueous bodily fluids and diffuses out of the polymer. This enables administration of the drug to be site-specific, limiting the exposure of the rest of the body to the drug.

The polymer used in the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The delivery of expandable stents is a specific example of a medical procedure that may involve the deployment of coated implants. Expandable stents are tube-like medical devices, typically made from stainless steel, Tantalum, Platinum or Nitinol alloys, designed to be placed within the inner walls of a lumen within the body of a patient. These stents are typically maneuvered to a desired location within a lumen of the patient's body and then expanded to provide internal support for the lumen. The stents may be self-expanding or, alternatively, may require external forces to expand them, such as by inflating a balloon attached to the distal end of the stent delivery catheter.

Where a stent or other medical device is to be coated, care must be taken during its manufacture to ensure the coating is properly applied and firmly adherent. When the amount of coating is insufficient or is depleted through stripping of poorly adherent coating during manufacture or deployment within the patient's body, the device's effectiveness may be compromised and additional risks may be inured into the procedure. For example, when the coating of the device includes a therapeutic, if some of the coating were removed during deployment, the therapeutic may no longer be able to be administered to the target site in a uniform and homogenous manner. Thus, some areas of the target site may receive high quantities of therapeutic while others may receive low quantities of therapeutic. Similarly, if the therapeutic is ripped from the device it can reduce or slow down the blood flowing past it, thereby increasing the threat of thrombosis or, if it becomes dislodged, the risk of embolisms. In certain circumstances, the removal and reinsertion of the device through a second medical procedure may be required where the coatings have been damaged or are defective.

The mechanical process of applying a coating onto a stent or other medical device may be accomplished in a variety of ways, including, for example, spraying the coating substance onto the device, so-called spin-dipping, i.e., dipping a spinning device into a coating solution to achieve the desired coating, and electrohydrodynamic fluid deposition, i.e., applying an electrical potential difference between a coating fluid and a target to cause the coating fluid to be discharged from the dispensing point and drawn toward the target.

Common to these processes is the need to apply the coating in a manner to ensure that an intact, robust coating of the desired thickness is formed on the stent. Obtaining a uniform coating often becomes difficult when working with coating fluids with low viscosities. In the case of electrohydrodynamic coating, when viscosity drops to a low viscosity, for example in the vicinity of one centipoise, it is difficult to control how much coating fluid is exposed to the electrohydrodynamic conditions. Non-uniform coating application is also a problem at very low coating fluid flow rates, where difficulty controlling conventional pumping means can result in erratic fluid flow from the coating dispenser. Lack of uniformity can be a problem as well where the coating fluid flow is applied to individual target work pieces in a start-stop fashion if the low viscosity coating fluid is given enough time to retreat from the coating fluid discharge point.

Further, obtaining a coating of the desired thickness requires precise coordination of the operating elements of the coating dispensing apparatus. In the case, for example, of an electrohydrodynamic coating system that employs a positive displacement pump to power the coating fluid dispenser, the electrohydrodynamic conditions must be closely matched to the pump in order to consistently achieve the desired uniform target coating. For example, if the electrohydrodynamic impulse is not applied as quickly as the pump is able to supply coating fluid to the dispensing head, excess fluid drops may form on the dispensing head and randomly alter the coating fluid deposition rate and spray pattern. Conversely, if the electrohydrodynamic impulse is faster than the pump can deliver coating fluid to the dispensing head, insufficient coating may result when the amount of coating material at the dispensing head is depleted by the electrohydrodynamic pulse before the pump can supply an adequate volume of additional coating fluid to the dispensing head. Under these conditions, it is difficult to achieve and sustain the required pump and electrohydrodynamic impulse coordination over the course of stent coating production runs.

Thus, there is a need for an apparatus and method for electrohydrodynamically applying a low viscosity coating fluid to a target such as a stent in a manner that results in a high quality coating of desired thickness, and preferably accomplishes this objective at high production rates.

SUMMARY OF THE INVENTION

The present invention is directed to an apparatus and a method for overcoming the foregoing disadvantages. Specifically, there is a provided an apparatus in which a target is held at a first electrical potential, and a coating fluid transporter configured to provide consistent flow of the coating material to a discharge point. When a second electrical potential is applied to the coating fluid, it is uniformly dispensed from the discharge point toward the target.

More specifically, the present invention includes a coating fluid transporter device, such as a wick, a siphon tube or a siphon tube containing a wick, that is sized to provide a stable fluid flow to the coating fluid spray dispenser when responding to flow demands generated by the application of the electrical potential, and to prevent the coating fluid from draining out of the transporter while the electrical potential is not being applied, such that the transporter remains primed and ready to apply the coating fluid to a subsequent target when the electrical potential is next applied.

In the case of a wick transporter, the coating fluid moves by capillary action from a reservoir end of the wick to a discharge end, where application of an electrical potential between the coating fluid and the target will cause the coating fluid to be discharged from the wick tip toward the target. Similarly, a siphon tube transporter of appropriate inner diameter for the viscosity of the coating fluid to be applied may be utilized to transport the coating fluid from the reservoir to the discharge point. A further embodiment features the combination of an appropriately-sized siphon tube with a wick within the tube's inner lumen along its interior to provide further enhanced coating fluid flow stability, particularly during intermittent coating fluid application.

The present invention thus provides the desired uniform coating fluid application to a target in a manner well suited to high volume, efficient coating of devices such as stents. In addition, due to the stability of coating fluid flow along an appropriately-sized wick or siphon tube, the coating fluid flow is self-regulating, with the supply being determined by the electrohydrodynamic conditions. The invention thereby may be used without additional flow control devices, such as pumps or flow control valves.

DETAILED DESCRIPTION

Figure 1:
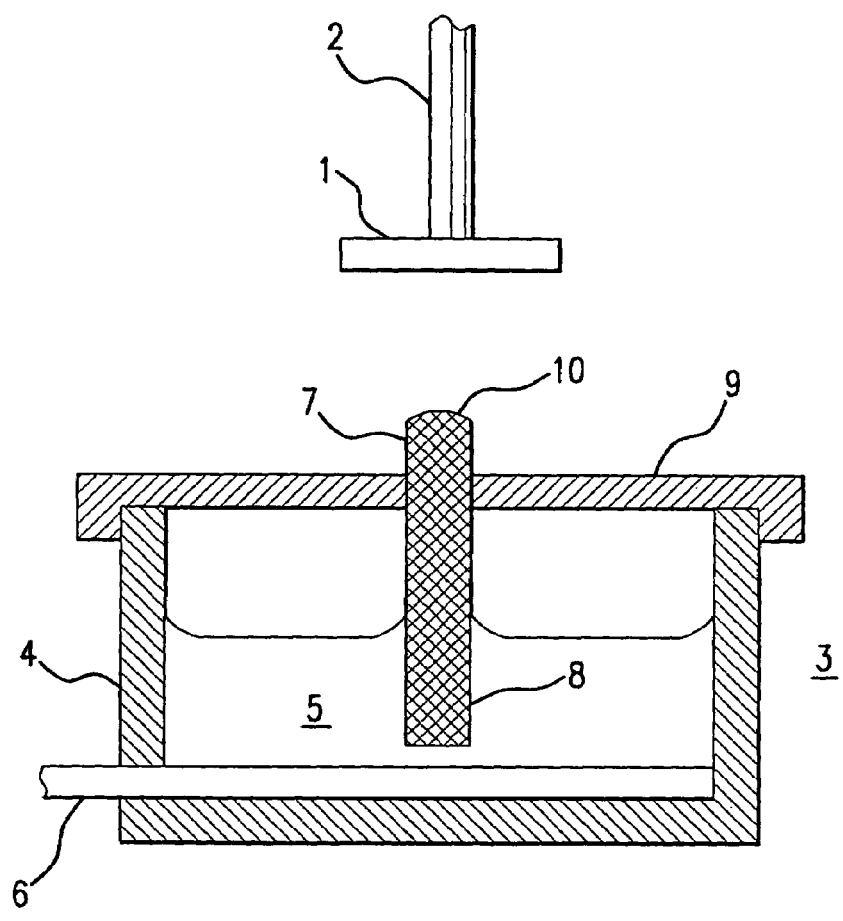
FIG. 1 is a schematic cross-section view of an electrohydrodynamic coating fluid delivery apparatus in accordance with a first embodiment of the present invention.

A first embodiment of the present invention is illustrated in FIG. 1. In this embodiment, a target 1 to be coated with a coating fluid is held by target holder 2. Target 1 in this instance is a stent that is to be coated with a therapeutic material. In addition to holding stent 1 in a position suitable for coating application, stent holder 2 functions as a electrode, and is maintained at a first electrical potential. Stent holder 2 may hold stent 1 by any number of means, such as by the stent holders described in U.S. patent application Ser. No. 10/198,094 (the disclosure of which is hereby expressly incorporated by reference herein), and may be adapted for use with high-speed automated stent handling apparatus.

Directly beneath stent 1 is a coating fluid spray dispensing device 3, schematically illustrated in FIG. 1 as comprising a coating fluid reservoir 4 holding a quantity of coating fluid 5, a solution of a therapeutic material in either an organic solvent or water with low viscosity (preferably below 100 centipoise), to be applied to the target stent. An electrode 6 is provided in contact with coating fluid 5 for establishing an electrical potential in the coating fluid. A wick 7 is provided in the reservoir with a first device end comprising a first wick surface 8 in contact with coating fluid 5. Wick 7 is supported in dispensing device 3 by a reservoir cover 9, which maintains wick 7 at a position directly below target stent 1. Wick 7 may be any of a number of well-known non-conductive fibrous or porous materials suitable for transporting liquid solutions via capillary action and resistant to degradation by the solution, e.g., and organic solvent-resistant engineered plastic. In this stent coating embodiment, wick 7 is cylindrical in shape. The diameter of wick 7 may be between approximately 0.5 mm and 3 mm, varied as desired to obtain a desired coating fluid flow rate. The distance between the dispensing end of the wick and the target may be maintained over a broad range, as the voltage difference that drives the electrohydrodynamic discharge of coating fluid toward the target may be readily adjusted to ensure the coating fluid reaches the target with a desired coating efficiency. Typical separation distances may be approximately 50-150 mm from the target. The wick 7 may alternatively be constructed of one or more tubes of very small diameter sufficient to transport the fluid via capillary action.

In operation, coating fluid 5 climbs along the structure of wick 7 via capillary action to reach the second or spray dispensing end 10 of wick 7. In the absence of the application of an electrical potential, surface tension forces between the coating fluid and the wick ensure that the coating fluid that reaches dispensing end 10 remains on wick 7. When coating material is to be applied to stent 1, an electrical potential is applied to reservoir electrode 6. Because coating fluid 5 is in direct contact with electrode 6, the coating fluid, including the coating fluid at wick dispensing end 10, is subjected to the same electrical potential. By maintaining the electrical potential on electrode 6 higher than the electrical potential on stent holder/electrode 2 (at a ground potential relative to electrode 6 in this embodiment), the coating fluid at wick dispensing end 10 is attracted to the lower potential at target stent 1. When the potential difference between wick end 10 and stent 1 becomes large enough, typically on the order of between 6,000-20,000 volts, a portion of coating fluid 5 leaves dispensing end 10 and travels toward stent 1 to apply the desired coating. In the present embodiment, a preferred voltage of 12,000 volts is maintained. As the coating fluid at wick end 10 is dispensed toward stent 1, additional coating fluid flows onto wick 7 at first surface 8 and moves toward wick end 10 to provide consistent fluid replenishment flow to end 10. The presence of reservoir cover 9 prevents bulk movement of coating fluid 5 in reservoir 4 directly toward stent 1.

The amount of coating fluid 5 delivered toward stent 1 may be adjusted by altering the length of time the electrical potential is applied to electrode 6, adjusting the potential difference between the first and second electrodes, and/or by adjusting the flow rate of the coating fluid up wick 7, for example by increasing or decreasing the cross-sectional area of the wick or changing the amount of wick surface area in contact with the coating fluid. This latter adjustment may be made by inserting wick 7 deeper into coating fluid 5 to increase the area of first surface 8 in contact with the fluid, or by altering the level of coating fluid 5 in reservoir 4.

After a predetermined time has lapsed, the electrical potential applied to electrode 6 is removed, eliminating the attraction of coating fluid 5 to stent 1, and thereby halting the coating fluid spray from dispensing end 10. When the electrical potential is removed from electrode 6, the momentum of the coating fluid flowing up the wick is immediately arrested by the surface tension of the coating fluid along the entire length of the wick 7 structure. As a result, there is no tendency for excess coating fluid to accumulate at, or leak from, wick dispensing end 10. The fluid surface tension also ensures that the coating fluid does not immediately retreat back toward first wick surface 8 and return to reservoir 4. Wick 7 therefore remains primed with coating fluid, ready for the next target coating operation, even where the fluid has a very low viscosity. The precise control of coating fluid by the present invention provides the additional benefit of permitting spray dispensing device 3 to be rapidly cycled in automated, high-speed target coating processes while still maintaining the desired precise and uniform coating application.

The present embodiment is not limited to target and spray device arrangements in which the target is held above the spray dispensing head, as the interaction of the surface tension forces between the wick and the coating fluid effectively eliminate undesired release of coating fluid when the electrical potential is not being applied to the electrode associated with the coating fluid supply. Thus, alternative orientations may be utilized, such as locating the coating fluid dispensing device above or alongside the target.

Figure 2:
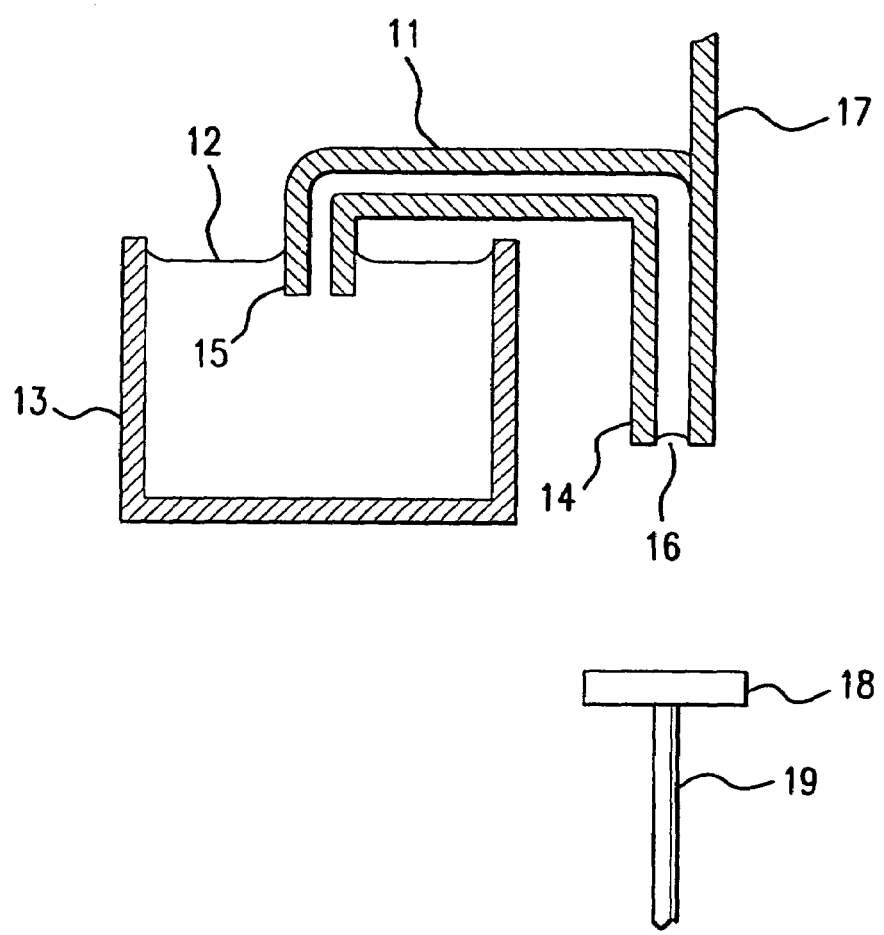
FIG. 2 is a schematic cross-section view of an electrohydrodynamic coating fluid delivery apparatus in accordance with a second embodiment of the present invention.
Figure 3:
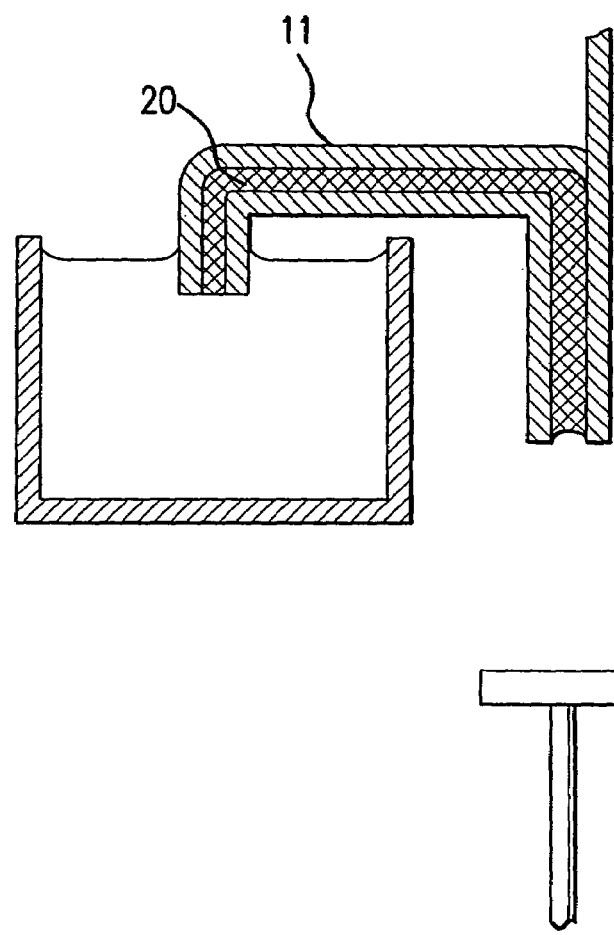
FIG. 3 is a schematic cross-section view of an electrohydrodynamic coating fluid delivery apparatus in accordance with a third embodiment of the present invention.
Figure 4:
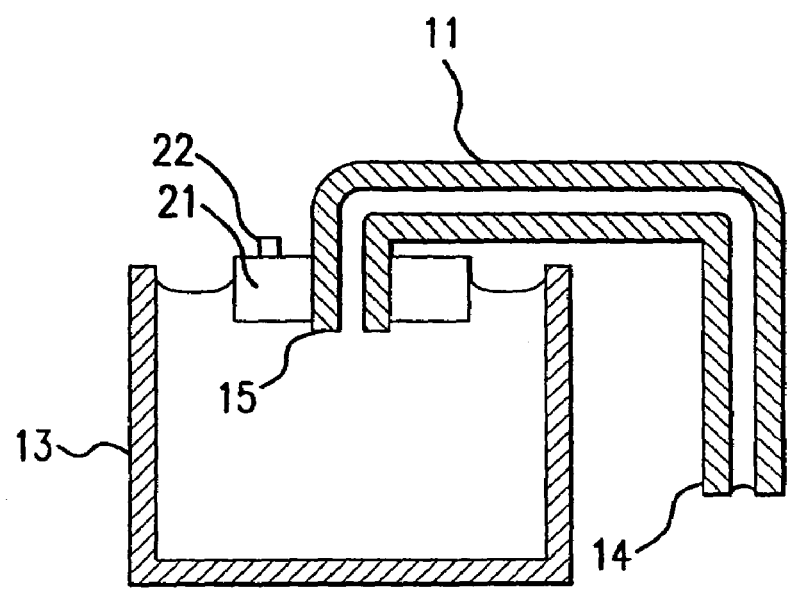
FIG. 4 is a schematic cross-section view of an electrohydrodynamic coating fluid delivery apparatus in accordance with a fourth third embodiment of the present invention.

A second embodiment of the present invention is illustrated in FIG. 2. In this embodiment, the coating fluid dispensing element of the first embodiment, wick 7, is replaced with a siphon tube 11. The inner diameter of siphon tube 11 must be sized sufficiently small to ensure that the surface tension forces in the fluid are not overcome, thereby avoiding formation of voids in the tube. The inner diameter must also be sufficiently small that the surface tension forces forming meniscus 16 at dispensing end 14 of siphon tube 11 are sufficient to preclude coating fluid leakage from the siphon tube when the apparatus is inactive.

In the present embodiment, the necessary inner diameter required to avoid loss of siphon will vary with the specific material used for tube 11 and the viscosity of the coating fluid. An example embodiment employing a non-metallic material such as a ceramic or plastic tube with an inner diameter of sufficient to prevent loss of siphon with a coating fluid with a viscosity on the order of one centipoise.

In order for the siphon tube to function properly, the level 12 of coating fluid in reservoir 13 should be maintained higher than the coating fluid dispensing end 14 of siphon tube 11. Inlet end 15 of siphon tube 11 is submerged into the coating fluid in reservoir 13. The height 12 of the coating fluid should be maintained above inlet end 15 to preclude loss of siphon from the reservoir end of siphon tube 11, and to ensure the meniscus formed at the opening of spray dispensing end 14 does not recede back into siphon tube 11.

As with the first embodiment, the flow rate of the coating fluid through the siphon tube fluid transporter may be adjusted by changing the height of coating fluid level 12 relative to siphon tube dispensing end 14. In addition, the flow rate can be adjusted by changing the height of siphon tube dispensing end 14. Care should be taken to ensure that dispensing end 14 is not so far below fluid level 12 that the surface tension forces meniscus 16 are overcome, such that the fluid begins to flow freely from dispensing end 14, or that conversely, dispensing end 14 is so high that surface tension forces between the fluid and the siphon tube surfaces are overcome, permitting the formation of siphon-breaking voids.

FIG. 2 also shows an alternative electrode arrangement, in which the electrode 17 that applies an electrical potential to the coating fluid is incorporated into dispensing end 14 in a manner that permits the coating fluid to be in direct contact with the electrode. As with the first embodiment, target 18 is held by target holder 19 at a lower potential than electrode 17. After the siphon tube has been initially primed with the coating fluid, an electrical potential is applied to electrode 17. This potential in turn is applied to the coating fluid immediately adjacent to dispensing end 14, resulting in the coating fluid being discharged from dispensing end 14 toward the target 18. As the coating fluid is being discharged from end 14, additional coating fluid is drawn into siphon inlet end 15 and through the siphon tube fluid transporter to sustain the coating flow from dispensing end 14 until the electrical potential is removed from electrode 17. When the electrical potential is removed from electrode 17, the surface tension forces between the small inner diameter tube and the coating fluid, including the surface tension forces at meniscus 16, prevent further discharge of coating fluid from dispensing end 14. The pressure differential and surface tension forces also resist retreat of the coating fluid back towards reservoir 13, thereby maintaining the siphon in siphon tube 11.

While the embodiment illustrated in FIG. 2 shows coating fluid dispensing end 14 arranged above target 18, alternative arrangements may be utilized, such as coating fluid dispensing toward an alongside target, so long as fluid level 12 is maintained above the fluid dispensing end 14.

As a further embodiment of the present invention, FIG. 3 illustrates a modification wherein wick material 20 is included within the lumen through siphon tube 11. The addition of wick 20 further enhances the stable, self-regulating flow properties of the siphon tube by providing significantly greater surface area for surface tension interaction between the low viscosity coating fluid and its transporter. This greater surface area enhances capillary flow through the tube during coating flow dispensing operations, enhances the arresting of fluid momentum when coating spray is halted, and discourages retreat of the coating fluid back to the reservoir when the apparatus is idle. Moreover, because the presence of wick material 20 decreases the widths of gaps between adjacent surfaces within siphon tube 11, it improves the siphon tube's resistance to depriming. This latter point is of particular usefulness, as it permits the use of a siphon tube with a larger inner diameter than would otherwise be possible with a low viscosity fluids in a hollow siphon tube. This in turn permits greater coating fluid flow rates during each target coating operation.

In a fourth embodiment of the present invention illustrated in FIG. 4, siphon tube 11 is coupled to a float 21 that rests upon the surface of the coating fluid in reservoir 13, and the electrical connection to the siphon tube electrode (not shown) is sufficiently flexible to permit siphon tube 11 to move vertically as the coating fluid level in reservoir 13 changes. If necessary, a counterweight 22 may be placed on or in float 21 to help counteract any tendency for siphon tube 11 to tip the float over.

With this embodiment, float 21 maintains siphon tube inlet end 15 at a constant depth relative to the surface of the coating fluid in reservoir 13, and accordingly maintains a constant height difference between the level of the coating fluid in reservoir 13 and siphon tube dispensing end 14. This latter fixed height difference results in the hydrostatic pressure at dispensing end 14 remaining constant as the depth of the coating fluid within the reservoir decreases, thereby improving the consistency of coating fluid discharge. Further, if siphon tube 11 is slidably mounted in float 21, the flow rate of coating fluid from discharge end 14 may be readily adjusted by sliding siphon tube inlet end 15 within float 21 to change its depth below the coating fluid surface. In a further variation of this embodiment, a mechanism may be provided to maintain a desired distance between the target and dispensing end 14 as coating fluid level in the reservoir decreases.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. For example, a stopcock may be placed in the siphon assembly to prevent the fluid flow to be turned on or off as desired, or, rather than float-mounting the siphon tube to maintain a constant hydrostatic pressure at dispensing end 14, a mechanism may be provided which automatically refills reservoir 13 to maintain a fixed coating fluid level in the reservoir. In addition, while the various elements of the disclosed invention are described and/or shown in various combinations and configurations, which are exemplary, other combinations and configurations, including more, less or only a single embodiment, are also within the spirit and scope of the present invention.

What is claimed is:

1. A method for electrohydrodynamic application of a coating fluid, comprising the steps of:

providing a coating fluid transporter with a first end in contact with coating fluid contained in a coating fluid reservoir, wherein the coating fluid contains a therapeutic agent;

transporting coating fluid through the coating fluid transporter from the first end to a second end of the transporter facing the target, wherein the coating fluid is transported by capillary action to provide a self-regulating fluid flow;

applying a first electrical potential to a target, wherein the target is a medical device; and applying a second electrical potential to the coating fluid in the coating fluid transporter, wherein the second electrical potential is sufficiently higher than the first electrical potential to cause coating fluid at the second end of the coating fluid transporter to be discharged toward the target.

2. The electrohydrodynamic coating method of claim 1, further comprising the step of:

controlling the application of the first and second electrical potentials to control the discharge of coating fluid from the second end of the coating fluid transporter toward the target.

3. The electrohydrodynamic coating method of claim 2, wherein the transporter is a wick.

4. The electrohydrodynamic coating method of claim 1, wherein the medical device is a stent.

5. The electrohydrodynamic coating method of claim 2, wherein the coating fluid transporter is a siphon tube, the first end comprises a first opening of the siphon tube in contact with the coating fluid in the coating fluid reservoir, the second end comprises a second opening of the siphon tube, and the second opening is lower than a coating fluid level in the reservoir, further comprising, prior to the step of applying a second potential to the coating fluid, the step of:

priming the siphon tube with the coating fluid.

6. The electrohydrodynamic coating method of claim 5, further comprising:

a wick within the siphon tube, wherein the wick is substantially the same length as the siphon tube.

7. A method for electrohydrodynamic application of a coating fluid, comprising the steps of:

providing a coating fluid transporter with a first end in contact with coating fluid contained in a coating fluid reservoir, wherein the coating fluid contains a therapeutic agent;

transporting coating fluid through the coating fluid transporter from the first end to a second end of the transporter facing the target, wherein the coating fluid is transported by siphoning action to provide a self-regulating fluid flow;

applying a first electrical potential to a target, wherein the target is a medical device; and applying a second electrical potential to the coating fluid in the coating fluid transporter, wherein the second electrical potential is sufficiently higher than the first electrical potential to cause coating fluid at the second end of the coating fluid transporter to be discharged toward the target.

8. The electrohydrodynamic coating method of claim 7, further comprising the step of:

controlling the application of the first and second electrical potentials to control the discharge of coating fluid from the second end of the coating fluid transporter toward the target.

9. The electrohydrodynamic coating method of claim 8, wherein the coating fluid transporter is a siphon tube, the first end comprises a first opening of the siphon tube in contact with the coating fluid in the coating fluid reservoir, the second end comprises a second opening of the siphon tube, and the second opening is positioned lower than a coating fluid level in the coating fluid reservoir, further comprising, prior to the step of applying a second potential to the coating fluid, the step of:

priming the siphon tube with the coating fluid.

10. The electrohydrodynamic coating method of claim 7, wherein the medical device is a stent.

11. The electrohydrodynamic coating method of claim 10, further comprising:

a wick within the siphon tube, wherein the wick is substantially the same length as the siphon tube.

* * * * *

UNITED STATES PATENT AND TRADEMARK OFFICE
CERTIFICATE OF CORRECTION

PATENT NO. : 7,261,915 B2  Page 1 of 1
APPLICATION NO. : 10/409590
DATED : August 28, 2007
INVENTOR(S) : Boulais et al.

It is certified that error appears in the above-identified patent and that said Letters Patent is hereby corrected as shown below:

Column 1, line 42, "andenoassociated" should be changed to --adeno-associated--;
Column 2, line 15-16, "nitorfurantoin" should be changed to --nitrofurantoin--;
Column 2, line 17, "lisidomine" should be changed to --linsidomine--;
Column 2, line 24, "Warafin" should be changed to --warfarin--;
Column 2, line 24, "Dicumarol" should be changed to --dicumarol--;
Column 2, line 26, "promotors" should be changed to --promoters--;
Column 2, line 28, "promotors" should be changed to --promoters--;
Column 3, line 9, "("BMP's")" should be changed to --(BMPs)--;
Column 3, line 12, "BMP's" should be changed to --BMPs--;
Column 3, line 19, "DNA's" should be changed to --DNAs--;
Column 4, lines 20-21, "(BAYHDROL®, etc.)" should be changed to --(BAYHDYROL®, etc.)--;
Column 4, line 23, "collage" should be changed to --collagen--;
Column 4, line 64, "device it" should be changed to --device, it--;
Column 5, line 64, "there is a provided" should be changed to --there is provided--;
Column 6, line 50, "a fourth third embodiment" should be changed to --a fourth embodiment--;
Column 7, line 14, "and organic" should be changed to --an organic--;
Column 8, line 47, "diameter of sufficient" should be changed to --diameter sufficient--;
Column 8, line 65, "forces meniscus" should be changed to --forces of meniscus--; and
Column 9, line 50, "fluids" should be changed to --fluid--.

Signed and Sealed this

Eleventh Day of November, 2008

JON W. DUDAS
*Director of the United States Patent and Trademark Office*